United States Patent [19]

Zine, Jr.

[11] 4,049,692

[45] Sept. 20, 1977

[54] STABILIZED BLOOD SEPARATING COMPOSITION

[75] Inventor: Anthony R. Zine, Jr., Corning, N.Y.

[73] Assignee: Corning Glass Works, Corning, N.Y.

[21] Appl. No.: 532,946

[22] Filed: Dec. 16, 1974

[51] Int. Cl.$^2$ ................................................. C07F 7/08
[52] U.S. Cl. .................. 260/448.2 B; 106/287 SB; 252/1; 252/316; 210/65; 210/83; 210/84; 233/1 A; 233/26
[58] Field of Search .............................. 260/448.2 B; 106/287 SB; 252/1, 316

[56] References Cited

U.S. PATENT DOCUMENTS

| | | | |
|---|---|---|---|
| 3,780,935 | 12/1973 | Lukacs et al. | 233/1 A |
| 4,018,564 | 4/1977 | Wright | 23/230 B |

Primary Examiner—Paul F. Shaver

Attorney, Agent, or Firm—James A. Giblin; Clinton S. Janes, Jr.; Clarence R. Patty, Jr.

[57] ABSTRACT

Gel-like composition useful for separating and partitioning whole blood into serum and clot portions. The composition has a specific gravity between that of the serum and clot portions such that, when centrifuged in the presence of whole blood, the composition forms a chemical and physical barrier between the serum and clot portions. The composition comprises, in combination, a silicone fluid, an inert siliceous filler dispersed therein, and a network former consisting of a polysiloxane-polyoxyalkyl copolymer which stabilizes the composition by minimizing and/or avoiding "wet out" of the siliceous filler with time. The composition has a viscosity within the range of about 200,000 to about 600,000 centistokes, preferably within the range of about 350,000 to about 450,000 centistokes.

4 Claims, No Drawings

STABILIZED BLOOD SEPARATING COMPOSITION

RELATED APPLICATION

U.S. patent application Ser. No. 314,270, now U.S. Pat. No. 3,852,194 filed Dec. 11, 1972 in the name of A. R. Zine, entitled "Apparatus and Method for Fluid Collection and Partitioning," and assigned to the present assignee.

BACKGROUND OF THE INVENTION

1. Field

This invention is concerned generally with blood collection test tubes or devices which are ultimately used to separate whole blood into serum and clot portions to facilitate analysis of the blood. Specifically, the invention is concerned with an improved gel-like composition which can be used in such blood collection tubes. Such compositions have physical and chemical properties which, in the presence of whole blood, permit the composition to be centrifuged to a position intermediate that of the serum and clot portions and, hence, form a barrier between the two portions.

2. Prior Art

Although the specific gravity of whole human blood is generally within the range of about 1.048 to 1.066, it has long been known that such blood can be readily centrifuged to effect a separation of the blood into two major components—a lighter serum portion having a specific gravity within the range of about 1.026 to 1.031 and a heavier clot portion, consisting mainly of red blood cells, having a specific gravity within the range of about 1.092 to 1.095. Such separations of whole blood into its two major components have greatly facilitated physical and chemical analyses of blood and, hence, assisted in the diagnosis and prognosis of many human ailments.

With the advent of modern sophisticated techniques for the analysis of various physical and chemical sub-components of blood, there has been a general recognition that simple centrifugation of whole blood into its two major components does not necessarily effect an ideal separation for analytical purposes. For example, even though simple centrifugation yields a gross separation of whole blood into serum and clot portions, there still exists an interface between the separated portions which, especially with time, results in the diffusion of various sub-components of one separated portion into the other. Such diffusion can affect the accuracy of various analyses.

In recent years, efforts have been made to overcome the problems associated with simple centrifugation. For example, it is now well known that various materials or devices having a specific gravity between those of the serum and clot portions can be used to assist in the separation and partitioning of the serum and clot portions. One such material consists of a gel-like, relatively inert, viscous composition having a specific gravity within the range of about 1.030 to about 1.050. Typical components of such a composition are a silicone fluid and a particulate silica filler. When whole blood, contained, for example, in a test tube, is centrifuged in the presence of such a composition, the composition, because of its specific gravity, tends to migrate to a position intermediate those of the serum and clot portions. Because of their viscous nature, such compositions ultimately assume a configuration which discourages and prevents formation of a serumclot interface, thereby forming a physical and chemical barrier between the serum and clot portions.

Various examples of such silica-silicone fluid compositions are well known in the art and described in detail, for example, in U.S. Pat. No. 3,780.935 to Lukacs and Jacoby and U.S. patent application Ser. No. 314,270, now U.S. Pat. No. 3,852,194 cited above, and incorporated herein by reference thereto. In the above cited patent and patent application, preferred compositions consist essentially of two components—a silicone fluid such as a dimethylpolysiloxane and very fine silica particles which act as a filler to assist in forming a gel-like material having an appropriate specific gravity. Such components tend to be preferred because they are essentially inert and, in combination, permit control of both specific gravity and viscosity.

In using such two component compositions, however, it has been found that, in time, the silicone fluid (e.g., a dimethylpolysiloxane) tends to react completely with the surfaces of the silica particles. This can result in a "wet out" of the particles. Very generally, the expression "wet out" refers to the tendency of such compositions to lose viscosity with time. Such a loss or reduction of viscosity leads to a reduction of the gel-like nature of the composition and the relative firmness of the composition is lessened. A very undesirable effort of wet out occurs when an attempt is made to pour off the upper serum portion of separated blood contained in a test tube. For example, as long as the test tube containing the separated blood components (with the gel-like barrier between) is maintained in an essentially vertical position, wet out poses no particular problem. However, as the tube is tilted to pour off the serum portion, a wetted out barrier has a tendency to slump, thus disturbing the previously maintained seal between the serum and clot portions. As the seal is disturbed, there forms an interface the serum and clot portions. Since such an interface permits diffusion or migration of various sub-components of the serum or clot portion into the other portion, the accuracy of various analyses can be adversely affected. It should be noted that undesirable slumping of the seal can occur even if a test tube containing such a seal between separated portions is jarred. From the foregoing, it can be appreciated that wet out of gel-like blood separating barriers is undesirable and the possibility of wet out occurring is a severe limitation on the storage stability of such gel-like compositions, whether stored in bulk or in individual evacuated blood collection containers.

It is known that such silicone fluid-silica compositions can be stabilized to some extent by adding such third components as gylcerol or even water. Both compounds have hydroxyl groups which tend to compete with the silicone fluid for surface bonding sites on the silica particles, thus tending to preclude the complete reaction of the silica surfaces with the silicone fluid which tends to result in wet out. It can be appreciated, however, that such compounds as glycerol and water are relatively small molecules which are not necessarily good network formers which assist in spacing individual silica particles apart from one another. Further, such compounds are not necessarily essentially inert with respect to the various sub-components of blood.

I have now found that there exists a group of compounds which, when added in relatively small amounts to a silicone fluid-silica gel-like composition, prolong the storage stability of such compositions and minimize the occurrence of wet out. The discovery is rather surprising since these third-component compounds have been used in entirely different applications in the past—as surfactants in the preparation of polyurethane foams. The compounds (copoylmers) and their use are described in detail below.

SUMMARY OF THE INVENTION

The improved gel-like thixotropic composition, useful in the separating and partitioning of whole blood into serum and clot portions, is a three-component system which maintains its viscosity for prolonged periods of time. This stabilized composition, which does not have a tendency to wet out, comprises in combination a silicone fluid, as essentially inert and particulate siliceous filler dispersed therein, and a network forming copolymer which is a polysiloxane-polyoxyalkyl copolymer existing in amounts sufficient to maintain an overall composition viscosity in the range of about 200,000 to 600,000 centistokes for periods of up to about one year. The overall composition must have a specific gravity within the range of 1.030 to about 1.090, preferably within the range of about 1.037 to 1.050. In a very preferred embodiment, the silicone fluid is a dimethylpolysiloxane, the siliceous filler consists of silica particles having an average primary particle diameter of about 18 millimicrons and a minimum surface area of about 80 m²/g, and the network former is represented by the formula

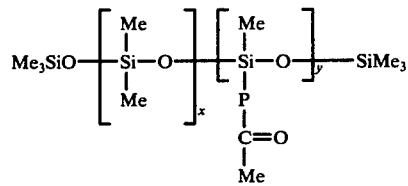

where the monomeric units are randomly distributed and

Me represents —CH$_3$;

$x$ represents a number between 80 and 120;

$y$ represents a number between 8 and 12;

P represents a polyoxyalkyl side chain represented by the formula

where the monomeric units are randomly distributed and $m$ represents a number between 20 and 30; and $n$ represents a number between 1 and 30.

The total three-component system must have a stable viscosity within the range of about 200,000 to about 600,000 centistokes at about room temperature. When the viscosity is below about 200,000 centistokes, the composition has a tendency to slump if contained in a test tube which is tilted to pour off serum. On the other hand, when the viscosity exceeds about 600,000, the composition is difficult to centrifuge with commonly available equipment. Preferably, the viscosity of the composition of this invention is within the range of about 350,000 to about 450,000 centistokes.

SPECIFIC EMBODIMENTS

The polysiloxane-polyoxyalkyl copolymers which can be used as network formers are well known and, as indicated above, have been used in other applications (e.g., surfactants in polyurethane foam production). Those skilled in the art will recognize that such copolymers can be made in a variety of ways as generally illustrated, for example, in U.S. Pat. Nos. 2,846,458 (Re. 27,727); 3,280,160; 3,402,192; 3,629,308; 3,629,310; and 3,637,738. Various polysiloxane-polyoxyalkyl copolymers which can be used are commercially available under a number of different product number designations such as copolymers known as DC-190, DC-192, and DC-194, commercially available from Dow Corning Corporation, Midland, Mich. Further, product information bulletins are available for such copolymers which bulletins describe in detail various properties of the copolymers.

In the examples below, three representative polysiloxane-polyoxyalkyl copolymers were used as network formers in gel-like silicone fluid-silica blood partitioning compositions. The stability of these compositions was compared with two components systesm (e.g., without the network former) by observing at what point in time there occurred a loss in viscosity below that which is useful in blood component partitioning applications (e.g., about 200,000 centistokes). Surprisingly, it was found that there ocurred essentially no loss in viscosity with time, when the network formers of the present invention were used. When such network formers were not used, under otherwise identical experimental conditions, viscosity drops to below about 200,000 centistokes were observed within only about 10 weeks. As shown below, viscosity increases above 600,000 centistokes were observed when such two component systems were stored in air due to moisture pick up.

Although the exact mechanism by which the polysiloxane polyoxyalkyl copolymers assist in minimizing or avoiding wet out is not fully understood, it can be appreciated that the very structure of such copolymers tend to make them ideal network formers. For example, the copolymers consist of two basic portions—a polysiloxane backbone portion and a plurality of polyether side chains which branch off of the polysiloxane backbone. The polysiloxane portion is relatively inert and quite compatible with the silicone fluid (e.g., dimethylpolysiloxane). On the other hand, the polyether side chains are capable of some hydrogen bonding at the surfaces of the silica particles. Since the polyether side chains tend to compete with the silicone fluid for surface bonding sites on the silica particles, the complete coverage of the silica surfaces by the silicone fluid is precluded. Hence, wet out tends to be avoided. Further, since the copolymeric network formers tend to have a relatively large molecular weight and size they assist in spacing the silica particles apart and thus further assure the maintenance of the gel-like nature of the overall composition.

In the examples below, polysiloxane-polyoxyalkyl copolymers having the structure described above were used as network formers in silicone fluid-silica gel-like compositions. As indicated above, the copolymers used are commercially available and known as DC-190, DC-192, and DC-194 surfactants. The copolymers are commonly referred to loosely as "silicone-glycol" copolymers to indicate starting materials used to prepare the copolymers. As described below, blood partitioning gel-like compositions were made with and without the addition of the third component network former. For the preferred network former, the stability of the composition, as measured by viscosity loss, was observed over a period of at least one year and essentially no loss in viscosity was observed, thus indicating substantially no likelihood of wet out for at least that period of time.

In preparing all compositions of the examples, the silicone fluid used was a dimethylpolysiloxane, made available by Dow Corning Corp. and identified as a 360 Series Silicone Fluid. It had a viscosity of about 12,500 centistokes at 25° C. and a specific gravity of 0.975. The silica particles consisted of very finely divided particles having a surface area of about 110 m²/g and a specific gravity of about 2.2. The silica particles were obtained from Degussa, Inc. and identified by the designation D-17. The silicone fluid and silica particles were intially mixed together in the indicated amounts to obtan a gel-like composition having an initial viscosity of about 200,000. Where indicated, the various network formers were titrated into the two-component systems in amounts sufficient to obtain a viscosity of about 375,000. Then, amounts of about 1.8 to 1.9 grams of the compositions were placed in blood collection test tubes of the type illustrated by FIG. 1 of Ser. No. 314,270. The tubes were then filled with about 10 ml. of whole blood and centrifuged at 1000 RCF for about 10 minutes, after which the stability (or tendency to wet out) of the intermediate composition was observed, by noting if the resultant seal slumped upon tipping the tube.

Example I

| Components | Parts by Weight | Approximate Percent by Weight |
| --- | --- | --- |
| Silicone Fluid | 100 | 86.9 |
| Silica | 15 | 13.0 |
| DC-190 | 0.0173 | 0.015 |

Example II

| Components | Parts by Weight | Approximate Percent by Weight |
| --- | --- | --- |
| Silicone Fluid | 100 | 85.5 |
| Silica | 17 | 14.5 |
| DC-192 | 0.0117 | 0.010 |

Example III

| Components | Parts by Weight | Approximate Percent by Weight |
| --- | --- | --- |
| Silicone Fluid | 100 | 86.9 |
| Silica | 15 | 13.0 |
| DC-194 | 0.0173 | 0.015 |

Control

| Components | Parts by Weight | Approximate Percent by Weight |
| --- | --- | --- |
| Silicone Fluid | 100 | 86.9 |
| Silica | 15 | 13.1 |
| (no network former) | 0 | 0 |

Comparison: The long term stability of the preferred composition of Example I is compared with that of the Control.

TABLE

| | Viscosity (CS) | | | |
| --- | --- | --- | --- | --- |
| | Example I | | Control | |
| Time (weeks) | Air | Vacuum | Air | Vacuum |
| 0 | 375M | 375M | 350M | 350M |
| 1 | 375 | 365 | 345 | 350 |
| 2 | 390 | 375 | 360 | 340 |
| 3 | 410 | 385 | 390 | 340 |
| 4 | 400 | 380 | 430 | 330 |
| 5 | 400 | 370 | 470 | 310 |
| 6 | 410 | 380 | 500 | 270 |
| 8 | 430 | 380 | 580 | 225 |
| 10 | 445 | 375 | 620 | 190 |
| 12 | (evacuated) 375 | 380 | * | * |
| 16 | 370 | 380 | | |
| 20 | 375 | 370 | | |
| 24 | 380 | 370 | | |
| 28 | 370 | 375 | | |
| 32 | 370 | 380 | | |
| 36 | 380 | 370 | | |
| 40 | 380 | 370 | | |
| 50 | 380 | 370 | | |
| 52 | 380 | 370 | | |

*Further data was not collected since these gels fell outside the range considered useful for this application (i.e., 200,000 to 600,000 centistokes).

With respect to the above table, it should be noted that the increse in viscosity with time of the control composition stored in air was due to the adsorption of water which, as indicated above, tends to act as a network former. This contribution due to water can also be seen in the slight increase in viscosity noted with time for the composition of Example I which was stored in air for the first 10 weeks. After 10 weeks, the composition of Example I which had been stored in air was stored in an evacuated state. This had the effect of removing the water which had been adsorbed from the air and an immediate drop in viscosity was noted from the 12th week on. As can be seen, this viscosity remained stable for at least 1 year. Although it can be seen that moisture adsorption is tolerable in the three-component composition of this invention, in very preferred embodiments, the composition is stored in an evacuated environment, preferably an evacuated blood collection test tube. In my examples, the designation vacuum means evacuated to about 5 to 7 inches of mercury. Such evacuation can be accomplished by conventional methods. In the case of blood collection tubes containing the three-components composition of this invention, the tubes commonly are evacuated to the extent needed to withdraw about 10 ml. of whole blood and then suitably stoppered to retain the evacuated state until used.

Very generally, my improved method of separating a sample of whole blood into serum and clot portions, using the three-component system of the present invention, comprises the steps of placing a quantity of whole blood into a container adapted to be centrifuged and containing the stabilized blood separating composition described above, and then centrifuging the blood into serum and clot portions under conditions sufficient to cause the composition to migrate to a position intermediate that of serum and clot portions of the blood, thereby forming an essentially inert and stable seal between the separated portions of the blood. In preferred embodiments, the blood container used is a test tube containing about 1.8 to about 1.9 grams of the composition described in Example I and, prior to insertion of the whole blood, the test tube is stoppered and evacuated to an extent sufficient to withdraw therein, via negative pressure within, about ten ml. of whole blood by conventional blood withdrawing techniques.

It can be appreciated that the above-described three-component composition of this invention and its use to separate serum and clot portions of whole blood, is subject to numerous modifications, within the scope of this disclosure. Accordingly, it is intended that the above-described examples should be construed as illus-

I claim:

1. In a thixotropic composition useful as a chemical and physical barrier between serum and clot portions of separated blood, the composition comprising a gel-like material having a specific gravity within the range of about 1.030 to 1.090 and consisting of a dimethylsiloxane silicone fluid having an inert siliceous filler dispersed therein, the improvement which comprises the addition of a network former in a quantity sufficient to maintain the viscosity of the composition within the range of 200,000 to 600,000 centistokes for prolonged periods of time, the network former consisting of a polysiloxane-polyoxyalkyl copolymer represented by the following formula

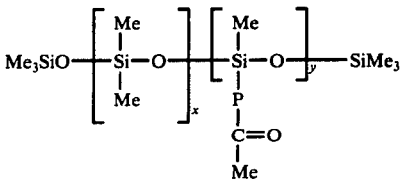

where the monomeric units are randomly distributed and

Me represents $-CH_3$;

$x$ represents a number between 80 and 120;

$y$ represents a number between 8 and 12;

P represents a polyoxyalkyl side chain represented by the formula

where the monomeric units are randomly distributed and $m$ represents a number between 20 and 30; and $n$ represents a number between 1 and 30.

2. The composition, as claimed in claim 1, wherein the specific gravity of the composition is within the range of about 1.037 and 1.050.

3. The composition, as claimed in claim 2, wherein the viscosity of the composition is within the range of about 350,000 to about 450,000 centistokes.

4. The composition, as claimed in claim 1, wherein the filler consists of silica particles having a surface area of at least about 80 $m^2/g$.

UNITED STATES PATENT AND TRADEMARK OFFICE
CERTIFICATE OF CORRECTION

PATENT NO. : 4,049,692
DATED : September 20, 1977
INVENTOR(S) : Anthony R. Zine, Jr.

It is certified that error appears in the above-identified patent and that said Letters Patent are hereby corrected as shown below:

Column 2, line 38, insert the word -- between -- immediately after the word interface and preceding the word the.

Column 5, line 14, change the word "obtan" to -- obtain -- .

Column 6, line 19, change the word "increse" to -- increase -- .

Signed and Sealed this

Seventeenth Day of May 1983

[SEAL]

*Attest:*

DONALD J. QUIGG

*Attesting Officer*     *Acting Commissioner of Patents and Trademarks*